United States Patent [19]

Swor

[11] Patent Number: 5,662,644

[45] Date of Patent: Sep. 2, 1997

[54] DERMATOLOGICAL LASER APPARATUS AND METHOD

[75] Inventor: William T. Swor, Sulphur Springs, Tex.

[73] Assignee: MDLT, Inc., Russellville, Ark.

[21] Appl. No.: 647,476

[22] Filed: May 14, 1996

[51] Int. Cl.$^6$ ................................................ A61B 17/36
[52] U.S. Cl. ................................. 606/9; 606/10; 606/13
[58] Field of Search ............................. 606/1, 9, 10, 11, 606/12, 13, 14, 15, 16, 17, 2

[56] References Cited

U.S. PATENT DOCUMENTS

| | | | |
|---|---|---|---|
| D. 351,911 | 10/1994 | Myers | D24/177 |
| 4,316,467 | 2/1982 | Muckerheide | |
| 4,525,842 | 7/1985 | Myers | 372/92 |
| 4,550,240 | 10/1985 | Toida et al. | 219/121 LS |
| 4,561,440 | 12/1985 | Kubo et al. | 128/395 |
| 4,573,465 | 3/1986 | Sugiyama et al. | 606/10 X |
| 4,601,288 | 7/1986 | Myers . | |
| 4,672,969 | 6/1987 | Dew | 606/11 X |
| 4,791,927 | 12/1988 | Menger | 606/10 X |
| 4,826,431 | 5/1989 | Fujimura et al. | 433/29 |
| 4,852,567 | 8/1989 | Sirofsky | 606/3 X |
| 4,866,720 | 9/1989 | Holly | 372/23 |
| 4,979,180 | 12/1990 | Muncheryan | 372/92 |
| 4,982,166 | 1/1991 | Morrow | 330/4.3 |
| 5,074,861 | 12/1991 | Schneider | 606/17 |
| 5,109,387 | 4/1992 | Garden et al. | 372/53 |
| 5,150,704 | 9/1992 | Tatebayashi et al. | 606/10 X |
| 5,151,909 | 9/1992 | Davenport et al. | 372/22 |
| 5,202,892 | 4/1993 | Harwick | 372/30 |
| 5,217,455 | 6/1993 | Tan | 606/9 |
| 5,243,615 | 9/1993 | Ortiz et al. | 372/34 |
| 5,290,273 | 3/1994 | Tan | 606/9 |
| 5,312,395 | 5/1994 | Tan et al. | 606/9 |
| 5,312,396 | 5/1994 | Feld et al. | 606/11 |
| 5,325,393 | 6/1994 | Nighan, Jr. et al. | 372/97 |
| 5,336,217 | 8/1994 | Buys et al. | 606/11 |
| 5,344,418 | 9/1994 | Ghaffari | 606/9 |
| 5,345,457 | 9/1994 | Zenzie et al. | 372/22 |
| 5,401,171 | 3/1995 | Paghdiwala | 433/215 |
| 5,405,368 | 4/1995 | Eckhouse | 607/88 |
| 5,461,692 | 10/1995 | Nagel | 385/127 |
| 5,468,238 | 11/1995 | Mersch | 606/15 |

OTHER PUBLICATIONS

Blueprint entitled "System, K–14", Kigre, Inc., Hilton Head Island, S.C. Oct. 29, 1992.
K–10 Series Sample Operator's Manual, Kigre, Inc., Hilton Head, S. C. undated.
"A Variable Pulsewidth Vascular System for Dermatology" Gustafsson et al., undated
"High–efficiency and compact blue source: intracavity frequency tripling by using LBO and BBO without the influence of birefringence," Wu, Riukun, Applied Optics 1993.
"Intracavity Fourth Harmonic Generation using Three Pieces of LBO in a Nd:YAG Laser," Wu et al., 1994.
Select 1000 Brochure, U.S. Dental Laser, Inc., Hilton Head Island, S.C.
Optometrech Systems brochure and drawing, undated, San Diego, CA
"Dental Laser Apparatus for Producing a Plurality of Wave Lengths with at Least One Laser Head in a Handpice," undated.

*Primary Examiner*—Jennifer Bahr
*Assistant Examiner*—Sonya Harris-Ogugua
*Attorney, Agent, or Firm*—Ray F. Cox, Jr.

[57] ABSTRACT

A dermatological laser apparatus and method in which at least three lasers generating at least three wavelengths of coherent radiation of known efficacy in the treatment of medical or dermatological conditions are provided in an integrated system. In the preferred embodiment, at least three lasers are combined in a console. The console houses some of the lasers along with cooling means, common power supplies, and control means to select among the available lasers. At least one of the lasers is generated in a handpiece. In an alternative embodiment, the handpiece is provided with means to accept interchangeable laser components.

13 Claims, 6 Drawing Sheets

FIG. 12

DERMATOLOGICAL LASER APPARATUS AND METHOD

BACKGROUND OF THE INVENTION

This invention relates to lasers used in dermatology applications and, in particular, to dermatological laser systems providing at least three laser wavelengths in an integrated functional system.

Lasers are recognized as effective treatment tools for a variety of dermatological conditions, including the treatment of port wine stain, the removal of tattoos, and face peels. Each type of dermatological condition, however, typically requires a different wavelength of laser radiation for effective treatment as well as different power intensities, pulse width, pulse rate and other characteristics of the laser radiation. The dermatologist is therefore faced with the necessity of purchasing several different types of lasers to accommodate the varying types of conditions that require treatment. Furthermore, the treatment of more than one condition of a single patient requires the dermatologist to employ several separate laser systems in a cumbersome and unsatisfactory fashion. This is an undesirable and inefficient methodology.

The integration of a plurality of lasers for dermatological applications is complicated by the types of delivery systems that are required for dermatological applications. For example, certain laser wavelengths at the desired power intensity cannot be transmitted by optical fibers, where other dermatologically useful wavelengths may most effectively be transmitted by optical fibers. Furthermore, some laser wavelengths may be generated within a manageable handpiece, while others require separate generation and delivery mechanisms. Some high powered laser generators require water cooling while others may require no cooling or only air cooling. The integration of a medically useful number of lasers in a single integrated functional package is particularly complicated for three or more lasers.

To the knowledge of the present inventor, no attempt has been made to provide an integrated system combining a plurality of at least three lasers for the treatment of dermatological conditions in a single package, nor has a method been suggested for employing a system having a plurality of at least three lasers in the treatment of dermatological conditions.

SUMMARY OF THE INVENTION

The present invention provides for a dermatological laser system having the capability of generating a plurality of at least three laser wavelengths of known efficacy in the treatment of dermatological conditions. The laser system used in the preferred embodiment of the method of the present invention is housed in a medical laser console of a type manufactured by Kigre, Inc., Hilton Head Island, S.C. This medical laser console, known as the K-14, has been modified for the application of the apparatus and method of the present invention. A similar medical laser console is the subject of U.S. Design Pat. No. Des. 351,911, the disclosure of which is incorporated herein by reference.

The preferred laser system contains at least three lasers in its basic configuration. Two of the laser beams are generated in a laser head assembly inside the unit. The third laser, called the Q-switched Infrared (QSIR), is generated in its separate handpiece. It is known to provide handpieces with internal laser generating means.

Of the two laser beams generated in the laser head assembly, the first is a commercially available 532 nm laser. The 532 nm wavelength may be generated by KTP frequency doubling of the 1064 nm output of a Nd:YAG laser or other technique well known in the art. The 532 nm laser beam is generated and discharged in an upward pointing direction. The upward pointing laser beam enters a delivery connector receptacle where it is reflected by a pair of mirrors 180° so that it exits the delivery connector receptacle in a downward pointing direction. This is desirable in that the optical delivery fiber is conveniently deployed for ease of use by the treating physician. The beam from the 532 nm laser is delivered to a silica fiber which is connected to the 532 nm connector at the outside bottom of the delivery connector receptacle. This silica fiber connects to the 532 nm handpiece. The 532 nm handpiece is held in a holster on the outside of the delivery connector receptacle.

The QSIR handpiece may also be held in a holster or other holder on the top of the delivery connector receptacle. The QSIR is a commercially available Nd:YAG crystal generating a 1064 nm wavelength. The QSIR laser has a cable which connects to a connector at the bottom of the delivery connector receptacle. This cable carries a power service and a hose for delivering air to the QSIR handpiece. An air pump and air line delivers air to the QSIR handpiece. The air pump is located inside at the bottom of the console. An air filter is attached to the air pump to provide filtered air. The air hose supplies the air from the pump to the delivery connector receptacle where it connects to the hose at the QSIR connector.

The third laser is a commercially available 2940 nm laser which is generated in the laser head assembly by an Er:YAG crystal. Like the 532 nm laser, this beam is also generated in an upward pointing direction. The 2940 nm laser beam, however, continues up through the delivery connector receptacle to a commercially available articulated arm and beam director. The articulated arm is provided with a number of internal mirrors to reflect the laser beam to the laser beam director.

Various versions of the articulated arm may be used in the practice of the present invention. One version is provided with a counterweight. A console pad provides convenient access to the controls for the system operation.

In the preferred embodiment of the present invention, the three lasers described above are provided in an integrated system for use in the present invention. Other arrangements of a plurality of laser generating means generating more than three laser wavelengths for treating dermatological conditions would also be suitable for the practice of the present invention. It should be understood that the particular wavelengths discussed above are not the only wavelengths that would be acceptable in the practice of the present invention. Other wavelengths and additional wavelengths may be employed. In addition to the treatment of the dermatological conditions listed above, the laser of the present invention may be employed for the treatment of other medical conditions. An example is the treatment of the condition of sleep apnea (or in a milder form, the problem of snoring). The problem is caused by an excess of tissue in the posterior of the throat, in particular in the uvula. Lasers of the same type as that known to be effective for the treatment of dermatological disorders (for example, a KTP frequency doubled output at a wavelength of 532 nm) are also effective in the treatment of sleep apnea. The procedure is to use a laser to remove and shrink tissues of the uvula and surrounding areas of the posterior of the throat. This and similar medical procedures are within the scope of the method and laser system of the present invention.

In certain alternative embodiments of the present invention, for example, the QSIR handpiece may be equipped with means to accommodate interchangeable laser generating modules for rapid and easy exchange of laser wavelengths as disclosed in U.S. Pat. Nos. 4,979,180 and 4,525,842. Handpieces may also incorporate more than one wavelength. In another embodiment of the present invention, additional laser wavelengths may be added to the three wavelengths described above; for example, a laser with a wavelength in the yellow portion of the spectrum.

It is therefore an object of the present invention to provide for the treatment of medical, and particularly dermatological, conditions using an integrated laser apparatus having laser means to generate a plurality of at least three laser wavelengths having known efficacy in the treatment of the medical or dermatological conditions.

It is also an object of the present invention to provide for a method of using a laser apparatus having a plurality of at least three laser means to treat medical or dermatological conditions.

Further objects and advantages of the present invention will become apparent from consideration of the detailed description of the preferred embodiment in conjunction with the drawings described as follows.

DETAILED DESCRIPTION OF THE PREFERRED EMBODIMENTS

The general appearance of the preferred laser system of the present invention may be described with reference to FIGS. 1–5, 7, and 8. A console 10 houses a plurality of lasers. As described more fully hereinafter, some portion of the lasers are disposed within the console 10, while other lasers have at least a portion located within the console 10 and the remaining portion attached to, but exterior of, the console 10. At least one of the lasers as described below is substantially housed within a handpiece. The console 10 not only provides the housing for some of the lasers but also provides the supporting systems for the lasers including power supply, controls, and cooling mechanism, all of which are more fully described below.

Each of the lasers employed in the present invention includes, as typical of all solid state lasers, a flash lamp, a power supply for driving the flash lamp, a laser medium, a highly reflective mirror and a partly transparent mirror.

Various types of flash lamps are known in the art. The laser medium may be any of a number of known suitable materials such as Nd:YAG and Er:YAG.

Figure 9:
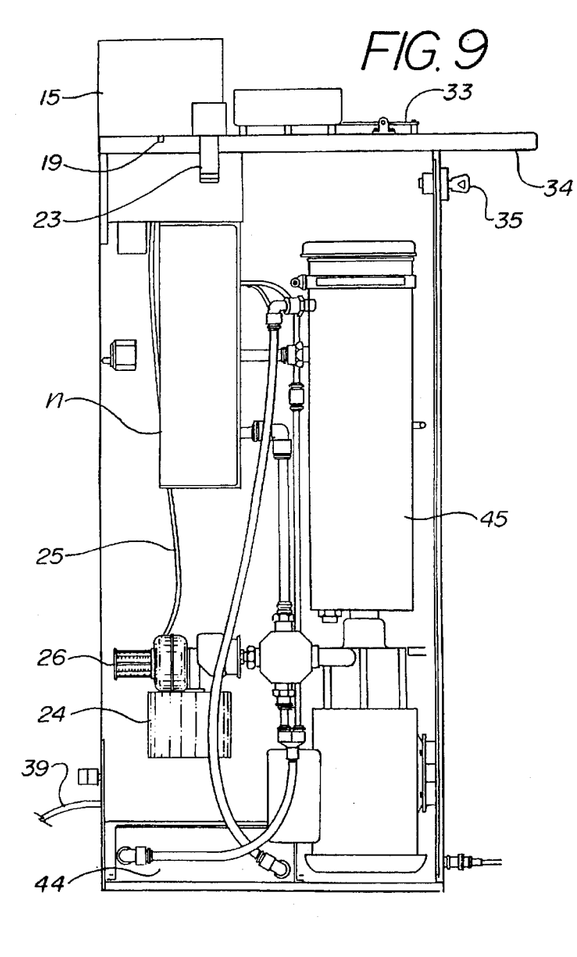
FIG. 9 is a left side elevation of the laser system console with the left side access panel open.
Figure 10:
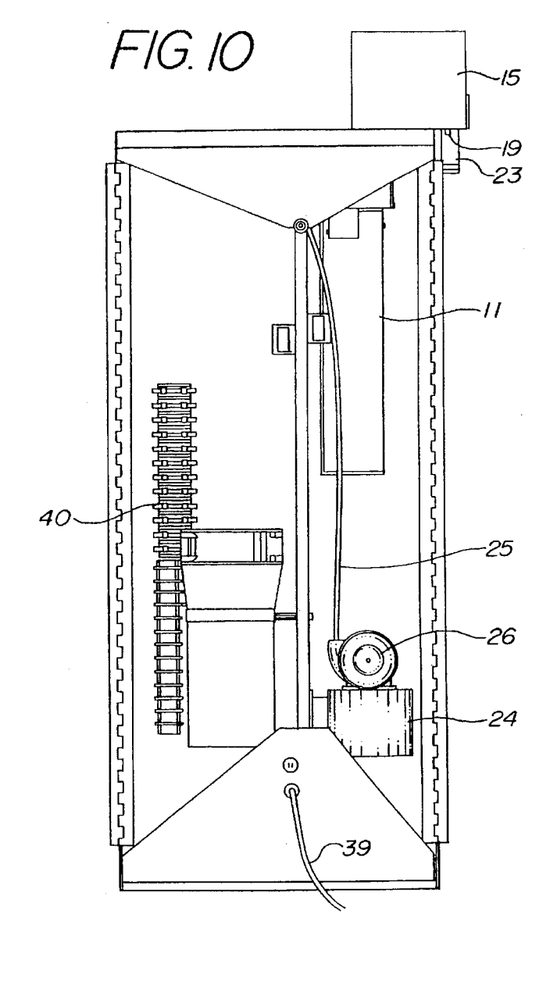
FIG. 10 is a rear elevation of the laser system console with the left side and the right side access panels open.
Figure 11:
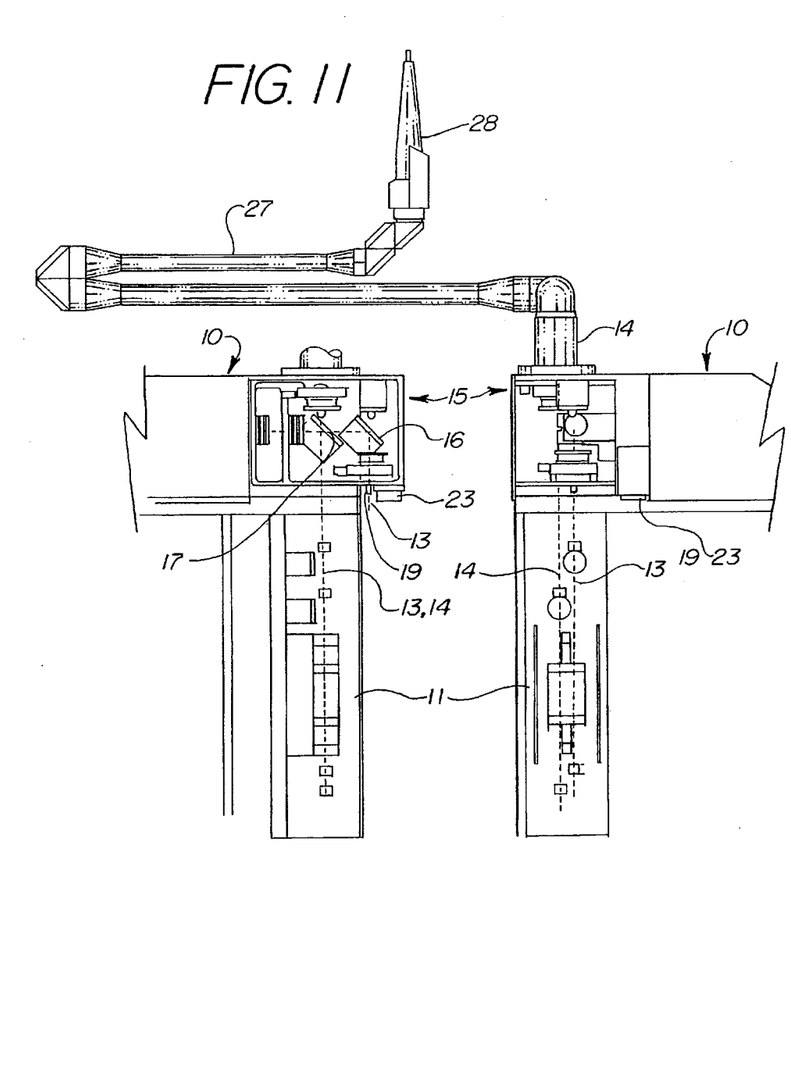
FIG. 11 comprises rear and left side sectional elevational views of the delivery connector receptacle.

The preferred laser system contains at least three lasers in its basic configuration. Two of the laser beams are generated in a laser head assembly 11 inside the console 10 as shown in FIGS. 9–11. The third laser, the Q-switched Infrared (QSIR), is generated in a separate QSIR handpiece 12.

Of the two laser beams 13, 14 generated in the laser head assembly 11, the first laser is a commercially available 532 nm laser. The 532 nm wavelength may be generated by KTP frequency doubling of the 1064 nm output of a Nd:YAG laser or other technique well known in the art. The 532 nm laser beam 13 is generated and discharged in an upward pointing direction. The upward pointing laser beam 13 enters a delivery connector receptacle 15 where it is reflected by a pair of mirrors 16, 17 through an angle of 180° so that it exits the delivery connector receptacle in a downward pointing direction. This is desirable in that the optical delivery fiber 18 is conveniently deployed for ease of use by the treating physician. The beam 13 from the 532 nm laser is delivered to a silica fiber 18 which is connected to the 532 nm connector 19 at the outside bottom of the delivery connector receptacle 15. This silica fiber 18 connects to the 532 nm handpiece 20. The 532 nm handpiece 20 is held in a holster 21 on the outside of the delivery connector receptacle 15.

The QSIR handpiece 12 may also be held in a holster or other holder on the top of the delivery connector receptacle 15. The QSIR is a commercially available Nd:YAG crystal generating a 1064 nm wavelength. Locating the QSIR head in the handpiece to deliver the Nd:YAG output is particularly advantageous since it avoids the need for transmitting the Nd:YAG output over a fiber optic cable. The handpiece 12 may be provided with a trigger switch operatively connected to a trigger transformer in a known manner. The handpiece 12 contains its own energy storage unit, spot lamp and associated optics, laser rod and flash lamp. A cooling lever is also supported to the handpiece 12. An interchangeable portion is also provided and may have a number of different geometries in order to accommodate various interchangeable laser wavelengths.

The QSIR laser is served by a cable 22 which connects to a cable connector 23 at the bottom of the delivery connector receptacle 15. The cable 22 carries a power service and a hose for delivering cooling air to the QSIR handpiece 12. Commercially available QSIR handpieces are equipped to receive a supply of cooling air and to exhaust the cooling air through the handpiece. With respect to FIGS. 9 and 10, an air pump 24 and air line 25 delivers cooling air to the delivery connector receptacle 15 and thence via the cable 22 to the QSIR handpiece 12. The air pump 24 is located inside at the bottom interior of the console 10. An air filter 26 is attached to the air pump 24 to provide filtered air.

The third laser is a commercially available 2940 nm laser which is generated in the laser head assembly 11 by an Er:YAG crystal. Like the 532 nm laser, the 2940 nm laser beam 14 is also generated in an upward pointing direction. The 2940 nm laser beam 14, however, continues up through the delivery connector receptacle 15 to a commercially available articulated arm 27 and beam director 28. For example, the articulated arm 27 may be of the type sold by Optometrech Systems, 9899 Hilbert St., Ste. A, San Diego, Calif. under the description of 16 mm clear aperture articulated arm. A suitable beam director is available from the same source. The articulated arm 27 is provided with a number of internal mirrors to reflect the laser beam 14 to the laser beam director 28. This arrangement is necessary when the wavelength or power intensity of the laser beam render the use of optical fibers undesirable.

Various versions of the articulated arm 27 may be used in the practice of the present invention. One version, illustrated in FIGS. 1–5, is provided with a counterweight 29.

Figure 7:
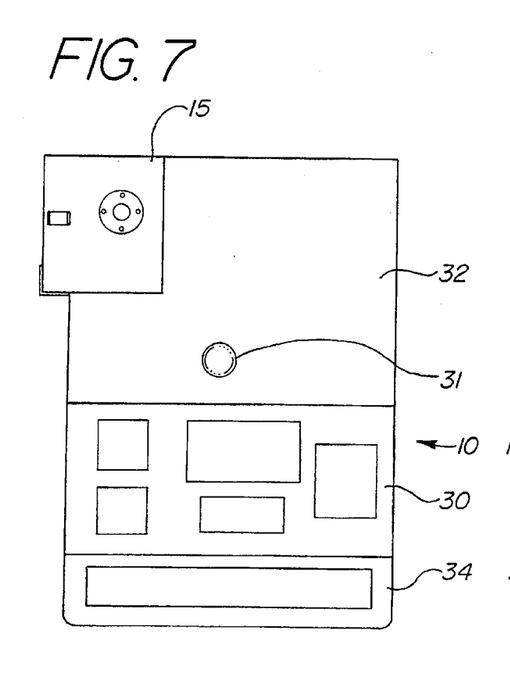
FIG. 7 is a top view of the laser system console with the top lid closed.
Figure 8:
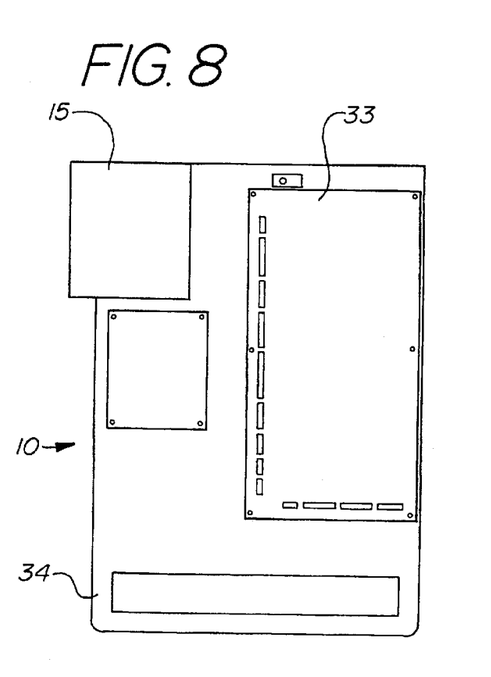
FIG. 8 is a top view of the laser system console with the top lid open. The top lid is removed for clarity.

The console 10 may be described with reference to FIGS. 1–5, 7, and 8. A console pad 30 as described more fully below provides convenient access to the controls for the system operation. An emergency stop button 31 is located on the top cover 32 of the console 10. The top cover 32 is hinged for access to the top interior of the console 10. FIG. 7 shows the top cover 32 in the closed position and FIG. 8 shows the top cover 32 in the open position revealing the top interior of the console 10. (The top cover 32 is shown removed for clarity.) With the top cover 32 open, the microprocessor board 33, which control the system operation, is accessible.

The console 10 is provided with a handle 34 for maneuvering the console 10 on caster wheels 38. Also conveniently located on the front of the console 10 is a key switch 35 and a BNC connector 36 for a foot switch 37, which allows hands free operation of the apparatus. A power supply cord 39 exits the rear of the console 10 and is connected to the internal power supply for the apparatus.

In certain alternative embodiments of the present invention, the QSIR handpiece may be equipped with means to accommodate interchangeable laser generating modules for rapid and easy exchange of laser wavelengths. Handpieces may also incorporate more than one wavelength. In another embodiment of the present invention, additional laser wavelengths may be added to the three wavelengths described above; for example, a laser with a wavelength in the yellow portion of the spectrum. Various other wavelengths are known to be efficacious in the practice of the present invention, including without limitation, wavelengths of the following magnitude (+\-10%): 755 nm, 585 nm, 355 nm, 694 nm, 2790 nm, 2100 nm, 1540 nm, 1320 nm, 266 nm, 213 nm, and 526 nm.

Figure 12:
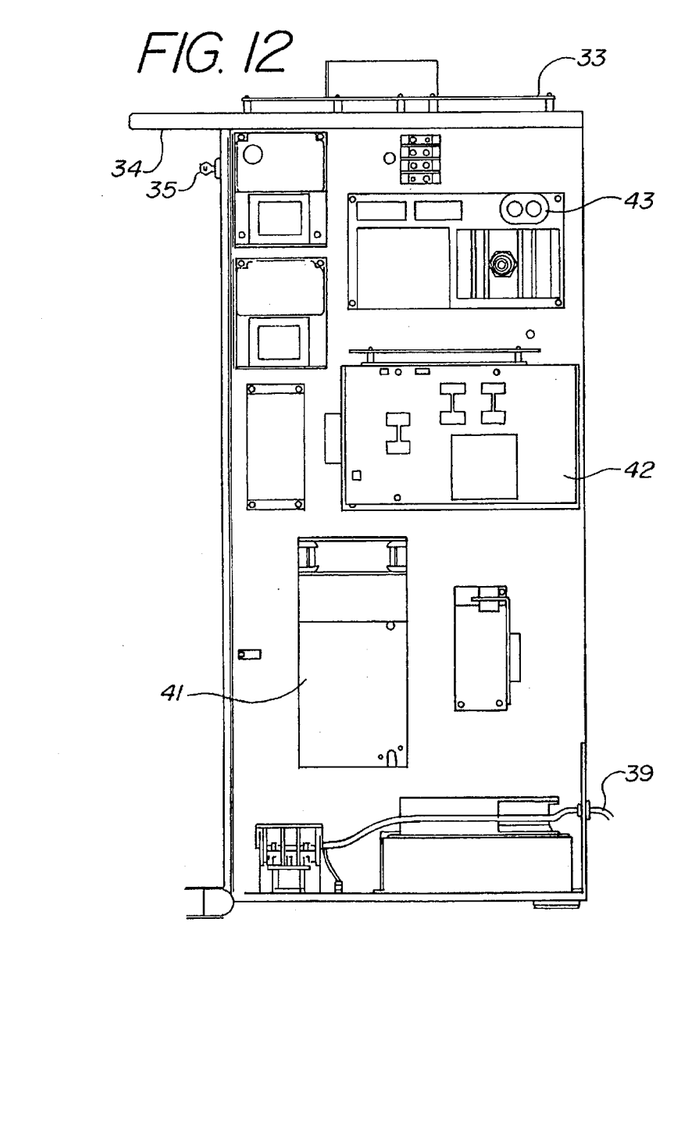
FIG. 12 is a right side elevational view of the laser system console with the right side access panel open.

A single power supply system supplying the plurality of lasers as shown in FIGS. 8, 10, and 12 is desirable. The power supply cord 39 delivers line voltage to an electrical distribution bus 40 for delivery of electrical power to the power supply system. The power supply system comprises a high voltage charging unit 41, an energy storage unit 42, and a pulse forming system 43 all operatively connected to supply the laser head assembly 11 under the control of the microprocessor 33. As shown in FIG. 9, the laser head assembly is cooled by a cooling system comprising a water-to-air heat exchanger 44 operatively connected to a water reservoir and pump assembly 45 which supplies cooling water to the laser head assembly 11. Both water and air cooling systems are known in the art and may be used in the practice of the invention.

Figure 1:
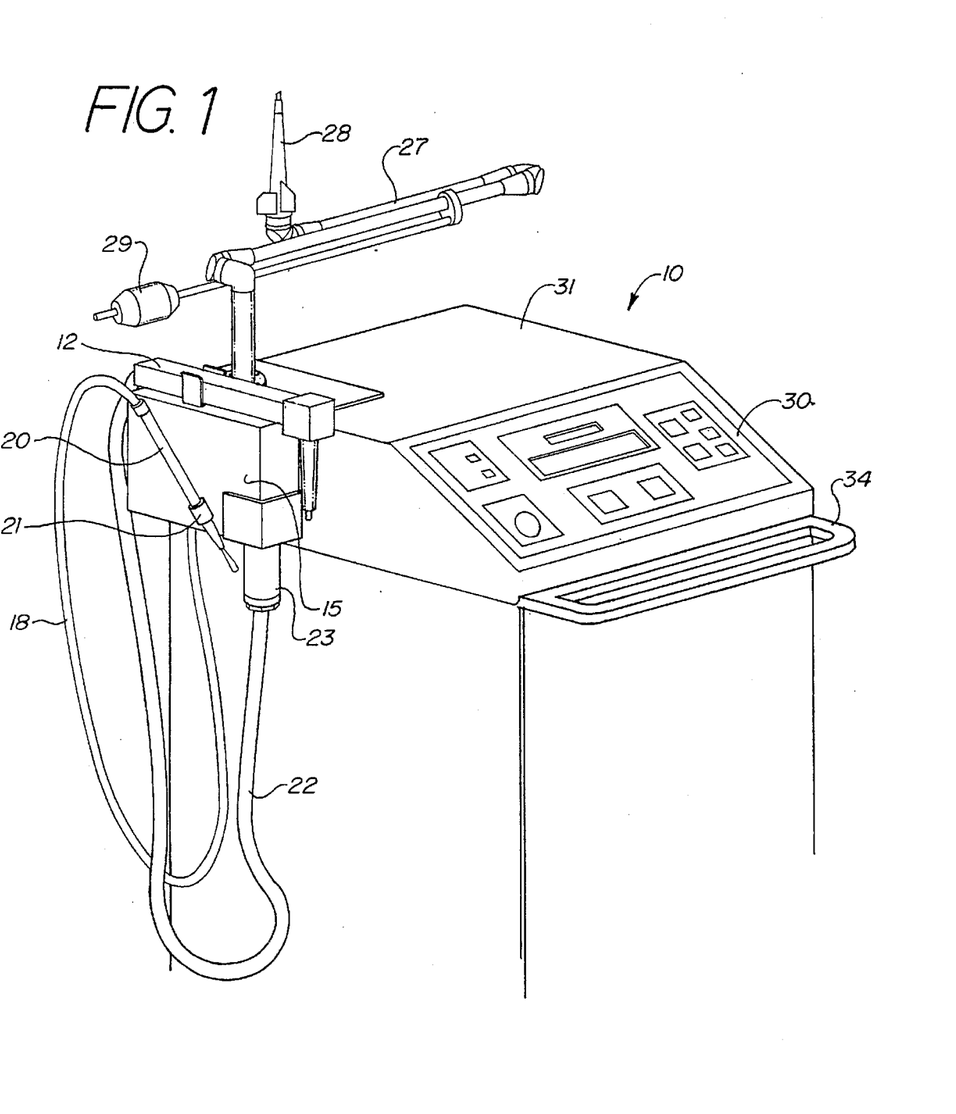
FIG. 1 is a perspective view of the laser system console.
Figure 2:
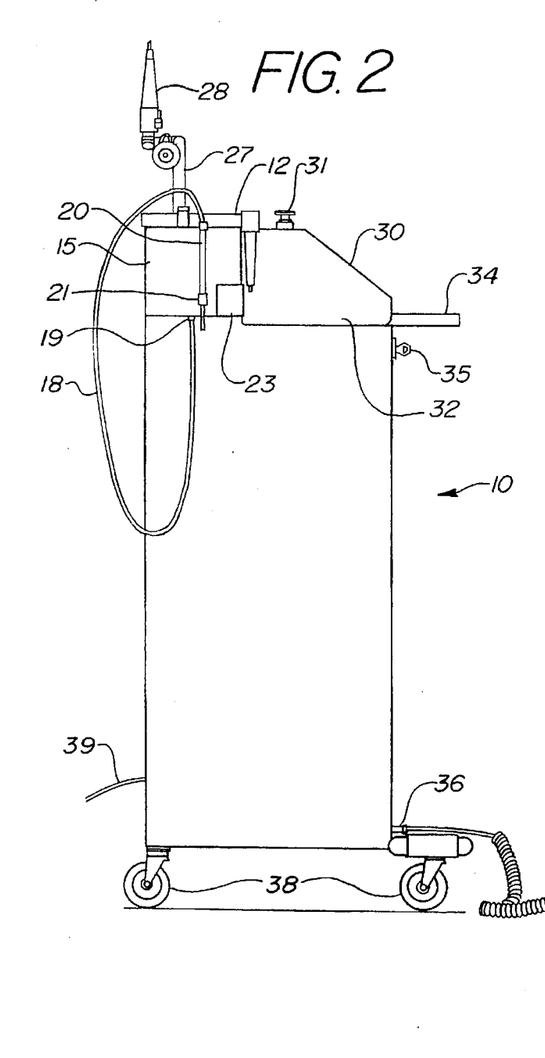
FIG. 2 is a left side elevation of the laser system console.
Figure 3:
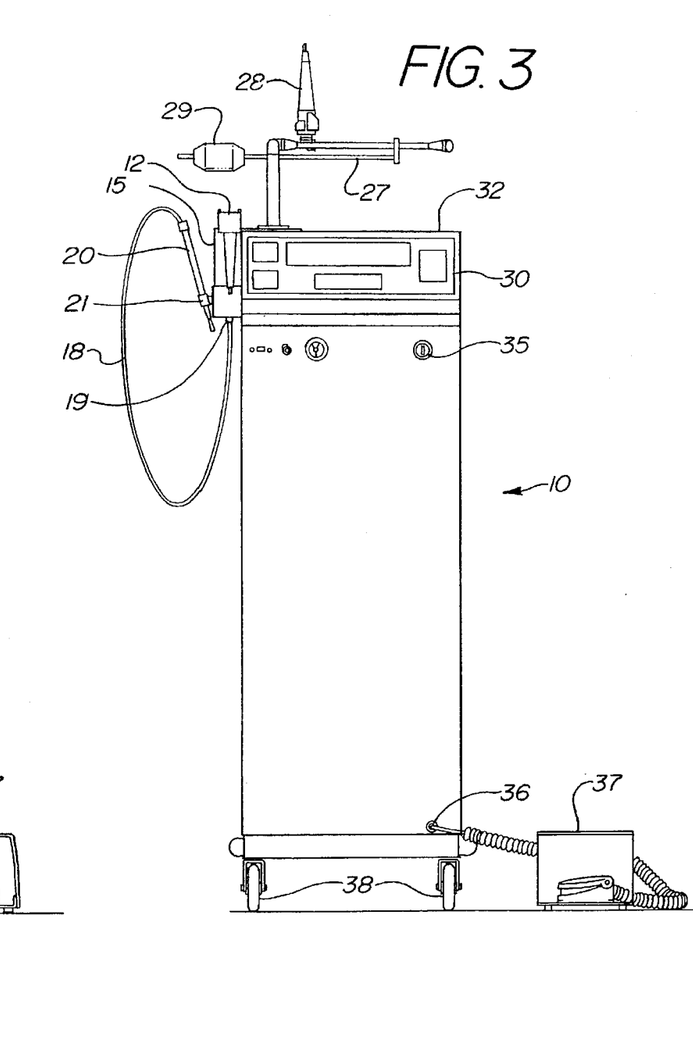
FIG. 3 is a front elevation of the laser system console.
Figure 4:
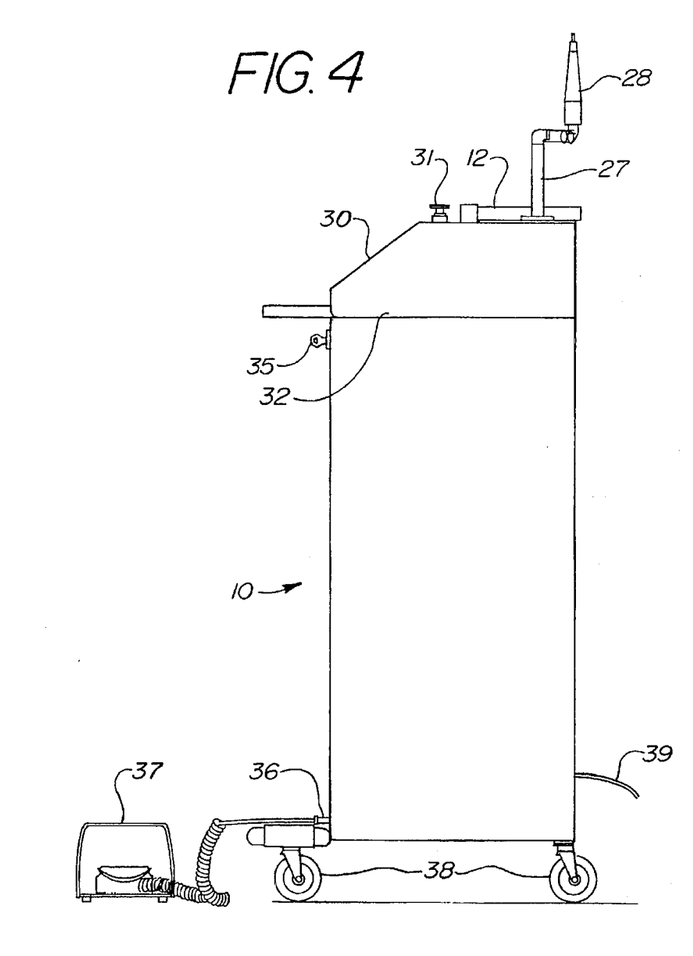
FIG. 4 is a right side elevation of the laser system console.
Figure 5:
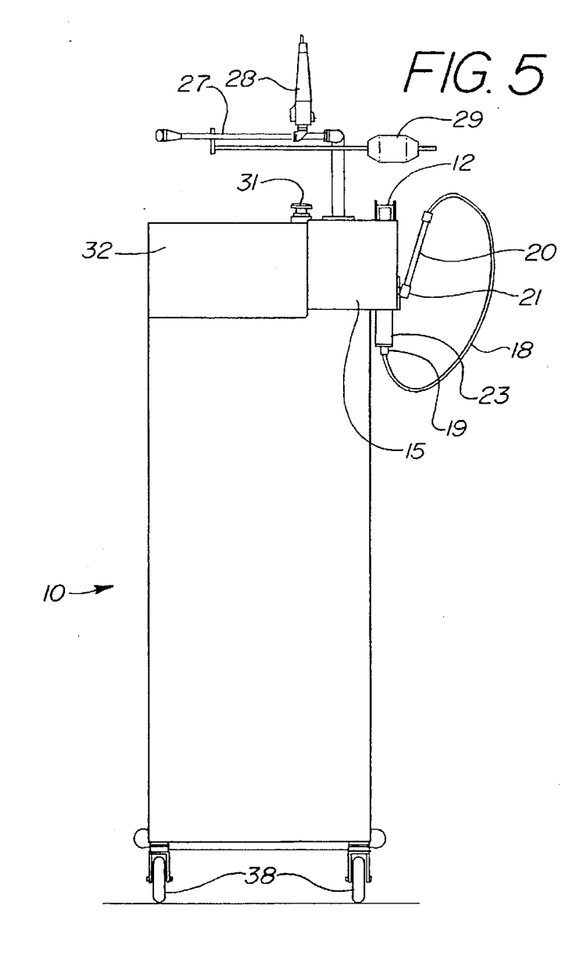
FIG. 5 is a rear elevation of the laser system console.
Figure 6:
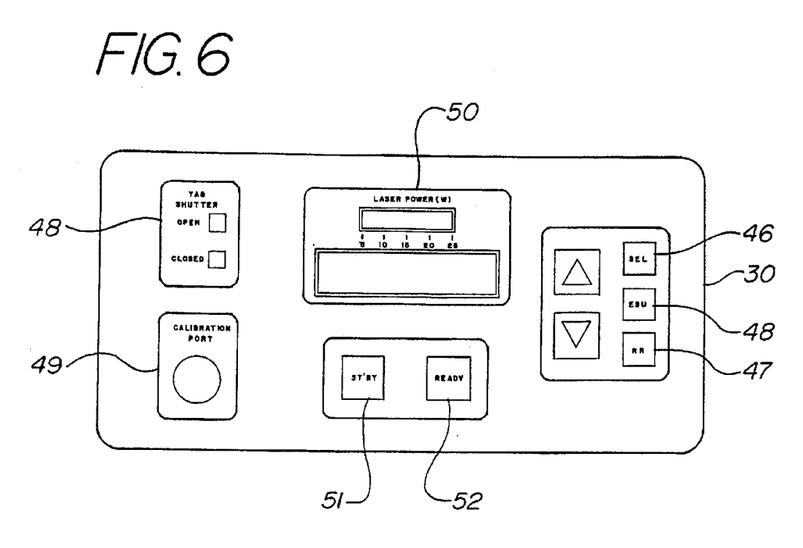
FIG. 6 is a diagram of the control panel of the laser system console.

As shown in FIG. 6, the console pad 30 allows control of the apparatus and in particular allows the selection of one of the plurality of lasers with the select (SEL) control 46 and the selection of various parameters; e.g., pulse width (PW), pulse repetition rate (PRR) and parameters associated with the energy storage unit (ESU). FIG. 6 illustrates exemplary controls such as the repetition rate (RR) control 47 and the energy storage unit (ESU) control 48, which are representative of the types of controls that may desirable but the scope of the invention is not limited thereto. The console pad 30 may also include various other controls, displays and selections. For example, there may be a shutter open/close control and indicator 48, a calibration port 49, a power selector and indicator 50, standby 51 and ready switches 52 and other controls and indicators. The console pad 30 provides microprocessor control of the lasers. In certain embodiments of the present invention, the console pad 30 may be a touchpad or touchscreen, technologies which are well known in the art.

A single variable pulse width driver may be employed for driving the plurality of lasers. Variable pulse width drivers are known which may be controlled to produce a first pulse width for driving a first type of laser and a second pulse width for driving a second type of laser. See, e.g., U.S. Pat. No. 5,202,892, the disclosure of which is incorporated herein by reference. The fluorescent lifetime of candidate laser materials and their corresponding wavelengths varies greatly, thus requiring a variable pulse width pump source for proper optimization. This feature also allows the user to optimize the laser's output pulse width for optimum depth of penetration and skin thermal relaxation rates. A switching mechanism, which may be under control of the microprocessor 33 and console pad 30 is used to selectively deliver the driver pulses to the selected laser. A high voltage switching mechanism may be used to selectively deliver the pulse width, repetition rate and energy desired from the lasers. This enables integration and optimization for a plurality of different laser heads. The energy storage unit 42 comprises a regulated capacitor bank. Various parameters may be adjustable, including peak energy, average power, pulse width and repetition rate.

The present invention has been described with respect to certain preferred and alternative embodiments which are considered to be exemplary only and not limiting to the full scope of the present invention as set forth in the appended claims.

What is claimed is:

1. A laser apparatus comprising:
   at least three laser means for producing at least three laser outputs;
   a plurality of handpieces;
   optical delivery means optically connected for receiving said laser outputs and delivering each of said laser outputs to a receiving end for receiving said laser output of a respective one of said plurality of handpieces;
   a console operatively connected to said at least three laser means and housing at least one of said laser means;
   and wherein at least one of said laser means is located in one of said handpieces.

2. The apparatus of claim 1 wherein said laser means comprises a first laser means generating a first laser output having a first wavelength, a second laser means generating a second laser output having a second wavelength and a third laser means generating a laser output having a third wavelength.

3. The apparatus of claim 2 wherein said first laser means and said second laser means are housed in said console and said third laser means is housed in one of said handpieces.

4. The apparatus of claim 3 wherein said first laser output travels along a first optical axis and said second laser output travels along a second optical axis and said optical delivery means comprises means for delivering one of said first and second laser outputs to a first handpiece and further wherein the other of said first and second laser outputs is delivered through said optical delivery means to a beam director operatively connected to an articulated arm affixed to said console.

5. The apparatus of claim 4 wherein said first laser means comprises an Nd:YAG laser having a frequency doubled wavelength of 532 nm, said second laser means comprises an Er:YAG laser having a wavelength of 2940 nm, and said third laser means comprises a Q-switched infrared laser having a wavelength of 1064 nm.

6. The apparatus of claim 5 wherein said first laser means and said second laser means are each driven by a common driver.

7. The apparatus of claim 6 wherein said first laser means and said second laser means are each driven by a common flash lamp driver, wherein said flash lamp driver comprises a variable pulse width driver.

8. The apparatus of claim 7 wherein a first cooling means housed in said console is provided for cooling both said first and second laser means.

9. The apparatus of claim 8 wherein said first cooling means comprises a water-to-air heat exchanger.

10. The apparatus of claim 9 wherein a second cooling means housed in said console is provide for cooling said third laser means.

11. The apparatus of claim 10 wherein said second cooling means comprises an air pump and means to deliver air from said air pump to said handpiece housing said third laser means.

12. The apparatus of claim 11 further comprising:

control means for controlling said laser means, wherein said control means comprises selection means for selecting at least one of said first, second, and third laser means.

13. The apparatus of claim 3 wherein said handpiece housing said third laser means is provided with means to accept interchangeable laser means.

* * * * *